United States Patent [19]
Suskin

[11] Patent Number: 4,844,890
[45] Date of Patent: * Jul. 4, 1989

[54] ROLL ON SHAVER AND FACIAL GROOMER

[76] Inventor: Ned Suskin, P.O. Box 25816, North Lauderdale, Fla. 33320

[*] Notice: The portion of the term of this patent subsequent to Oct. 4, 2005 has been disclaimed.

[21] Appl. No.: 693,599

[22] Filed: Jan. 22, 1985

Related U.S. Application Data

[63] Continuation-in-part of Ser. No. 289,039, Jul. 31, 1981, abandoned.

[51] Int. Cl.⁴ .................. A61K 7/15; A61K 7/42; A61K 7/44; B23F 19/06
[52] U.S. Cl. .................................. 424/73; 409/37; 424/59; 424/60; 514/937
[58] Field of Search .................. 424/73; 514/937; 409/37

[56] References Cited

U.S. PATENT DOCUMENTS

| 3,932,622 | 1/1976 | Friedman et al. | 514/937 |
| 3,988,436 | 10/1976 | Loo | 514/937 |
| 4,032,630 | 6/1977 | Osberghaus | 424/73 |
| 4,035,477 | 6/1977 | Schubert | 424/73 |
| 4,036,951 | 7/1977 | Halpern et al. | 514/937 |
| 4,104,403 | 8/1978 | Barker et al. | 514/937 |
| 4,128,631 | 12/1978 | Lundmark et al. | 424/73 |
| 4,145,411 | 3/1979 | Mende | 424/73 |

Primary Examiner—Dale R. Ore

[57] ABSTRACT

A composition for use as a grooming and a facial shaving lotion that consists essentially of transterificated wheat germ oil, cocomide dea used as an emulsifier; olet-2 which is a polyethylene glycol ether used as a surfactant and octyl hydroxy-stearate used as a refatting agent. A suitable sunscreening agent such as para-aminobenzoate may be added and perfume to provide a pleasing fragrance. Ches 500 may be added as an emulsion stabilizer.

12 Claims, 1 Drawing Sheet

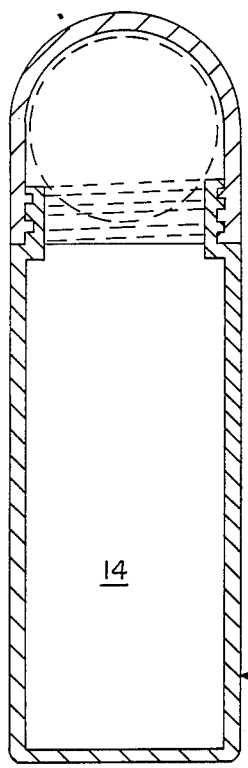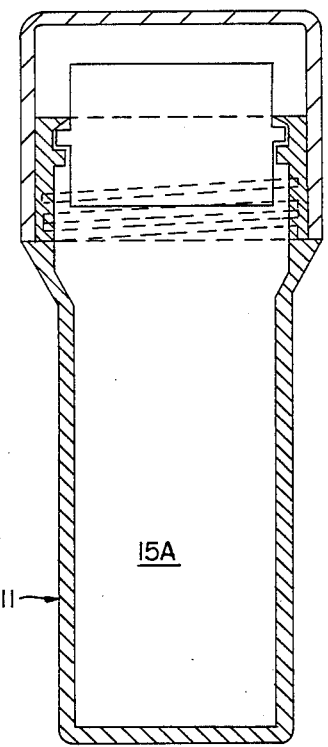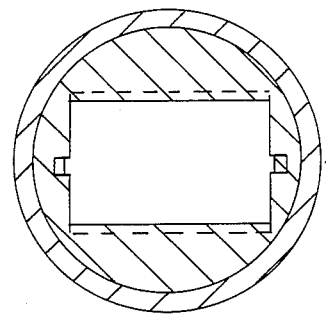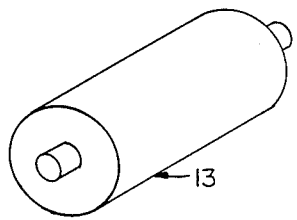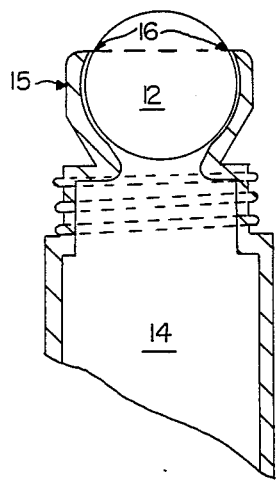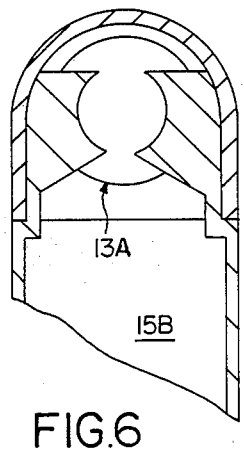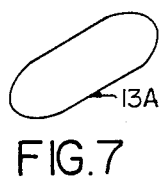

ROLL ON SHAVER AND FACIAL GROOMER

BACKGROUND OF THE INVENTION

This is a Continuation-in-Part of patent application, Ser. No. 06/289,039, filed July 31, 1981, now abandoned.

The invention relates to facial grooming substances, and more particularly, to a lotion that is suitable for being applied to the skin in preparation for shaving and for facial grooming.

PRIOR ART

Facial grooming agents have in the past been disclosed by a number of inventors.

U.S. Pat. No. 3,932,622 discloses a skin moisturizing composition.

U.S. Pat. No. 3,988,436 discloses a facial sunscreen method using a rice bran oil.

U.S. Pat. No. 4,032,630 discloses a skin treating agent containing polyhydroxy-polycarboxylate polymers.

U.S. Pat. No. 4,035,477 discloses a pressurized foaming shaving composition and method of making same.

U.S. Pat. No. 4,036,951 discloses an ultraviolet filtration with certain aminosalicyclic acid esters.

U.S. Pat. No. 4,145,411 discloses a pressurized foaming shaving composition with an anionic surface active agent.

U.S. Pat. No. 4,081,484 discloses a method for preparing carborane.

U.S. Pat. No. 4,104,403 discloses water-oil emulsions and method for preparing same.

U.S. Pat. No. 4,128,631 discloses a method for imparting lubricity to keratinous substances and mucuous membrances.

SUMMARY OF THE INVENTION

The invention is a roll-on shaving and facial lotion, also usable as a shaving and skin conditioner, and a cosmetologent that is a complete all-in-one facial grooming agent. The product is suitable for application by a roll-on applicator. The product is a latherless lotion that provides visibility during shaving and serves as a shaving vehicle, and it also may serve as an aftershave and a skin conditioner, that may advantageously be contained in a conventional roll-on dispenser. The product, according to the teachings of the invention, is a composition that essentially consists of Octyl Hydroxstearate, (Skin Conditioner); Cocamide Dea, (surfactant; Oleth-2 (binder); Perfume (Fragrance); Wheat Germ Glycerides (Vita-Cos Anti-Toxicant & Healant) mechanically combined to form a semi-liquid composition of a viscosity that is suitable for application by a roll-on applicator. The product may also be applied by other suitable methods of dispensing, such as a roll-up tube, by hand, by a brush, or by an aerosol dispenser.

In case the product is to be dispensed by an aerosol dispenser, more liquid in the form of water may be added to the composition to reduce the viscosity and the composition will be enclosed in an aerosol dispenser of conventional construction with a conventional gaseous propellant.

In still another embodiment, the product may be combined with a sun-screening agent such as para-aminobenzoate, rice-bran oil, or any other suitable sun-screening agent.

BRIEF DESCRIPTION OF THE FIGURES

FIG. 1 is an elevational cross-sectional view of the container for a spherical roller for a roll-on applicator;

FIG. 2 is an elevational cross-sectional view of the container for a cylindrical roller for a roll-on applicator;

FIG. 3 is a top-down view of a roll-on applicator with a cylindrical roller, taken along the line 3—3 of FIG. 2;

FIG. 4 is a perspective view of a roll-on cylinder;

FIG. 5 shows a vertical cross-section of the neck and spherical roller of an applicator; and FIG. 6 shows a vertical cross-section of the neck and spherical roller of an applicator.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The facial lotion according to the present invention may be produced by mechanically combining the basic ingredients in any one of a number of different ratios.

The ingredients include:

(a) transesterificated wheat germ oil with glycerine to form wheat germ glycerides with 30-40% monoglycerides, diglycerides, and triglycerides about 0.05% BHT (Butylated Hydroxytoluene) and 0.255 di-alpha tocopherol acetate (Vitamin E) as antioxidants. Wheat germ glycerides were tested in rabbits for dermatoxicity by the Draise method and determined not to be a primary irritant. This ingredient is unique because it is both hydrophyllic, and oleophyllic, ideal for skin penetration and utilization, and serves to maintain the tone of the skin. It is also a very effective skin lubricant that lubricates without a greasy feel, and aids in maintaining normal moisture control, and helps in smoothing skin blemishes by increasing skin elasticity, plus natural Vitamin E as an antiirritant. The wheat germ glycerides provide better performance, and their benefits appear to surpass all present day shave and skin products. No other grooming product has this very desirable skin enhancing ingredient.

(b) Cocamide Dea is a mixture of ethanolamides of coconut acid conforming to formula

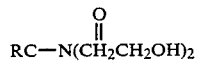

$$RC-N(CH_2CH_2OH)_2$$

wherein RCO represents the coconut acid radical. Cocamide Dea is a vehicle used as an emulsifier, dispersant, thickener and an alkanolamide that aids in the coupling, and combining of the emulsion.

(c) Oleth-2. A polyethylene glycol ether of oleyl alcohol according to the formula: $CH_3 (CH_2) CH=CH (CH_2)_7 CH_2 (OCH_2 CH_2) Oh$ wherein N is an integer with an average value of 2. This surfactant is used to further aid in bringing all phases together by making them mutually compatible.

(d) Octyl Hydroxystearate, which is a refatting agent that exhibits the characteristic of preventing the defatting effect of detergent-containing materials, and in some cases causes an increase in the amount of surface fat. The primary dermal irritation index of Octyl- Hydroxstearate has indicated that this material is considered to be a non-irritant according to test patches on rabbits. This emollient is basically an alkyl branched aliphatic compound with the unique property of increasing the water vapor porosity of the fatty compounds. The branched chain esters achieve the desired objectives of smooth after-feel with unique emolliency, and refatting characterists. Water may optionally be added in order to reduce cost. If water is added, the following ingredient (e) is also used:

(e) Ches 500 may be included as a cold hot emulsion stabilizing system, and is a GRAS emulsifier added to stabilize the long term oil-water emulsion. It is made by WICKHEN Corp. and creates a smooth silky feel, but other suitable emulsion stabilizers can also be used. Further included in the product may be 2-3% perfume. Sunscreens, and suntanners are optional features to be added to varying degrees. A main characteristic and advantage of the product is a latherless lotion for improved shaving and visibility during shaving, leaving no foam residue, so no after wash is necessary.

The shaving lotion according to the invention is advantageously produced as follows:

First a mixture consisting of 20% by weight of ethanolamides of coconut acid (cocoamide dea) with 14% by weight of polyoxyethylene oleyl ether is prepared. The mixture is stirred until a uniform mixture is obtained;

next, slowly, 60% by weight of octyl hydroxystearate is added, by continued stirring until the mixture is clear;

next, gently warm the mixture while stirring, and add 1.5% by weight of wheat germ glycerides; and if desired, add perfume, e.g. Essence de Pierre Cardin or any desirable perfume, in the amount of 4.5% by weight, or less, while continuously stirring until the mixture is completely homogenous and uniform throughout.

The wheat germ glycerides are specially transesterified wheat germ oils with glycerides to form wheat germ glycerides with 30%-40% monoglyceride, and are uniquely effective skin lubricants which provide a simple method to attain the maximum lubricant benefit from a minimum of effort and cost. Combined with the shaving lotion according to the invention, the lotion is especially suited for application by means of a roll-on applicator. Furthermore, the composition is a latherless, waterless lotion which uniquely conditions the skin and beard for shaving while leaving the skin of the shaved areas visible while shaving them.

Further still, in the application of the lotion by means of a roll-on applicator of the type shown in the figures of the drawing, the skin is being massaged and stroked in a way that has been found to be highly beneficial and envigorating and helpful in retarding the wrinkling and aging process of the epidermis of the skin.

Further still, after shaving, when the residual film of the lotion is left on the skin, it contributes to moisturizing the skin, which further enhances its appearance.

The optional addition of a sunscreen ingredient to the composition contributes to the inhibition of ultraviolet exposure, which also is beneficial in preventing aging of the skin.

The ingredients listed hereinabove as (a), (b), (c), (d) and (e) may alternatively be combined in any suitable ratios by straight mixing of the ingredients. Water may be added until a suitably viscous consistency is attained.

Various very effective ratios of the ingredients have been determined as shown in the following examples:

| Example 1 | |
|---|---|
| Ingredient | Parts by Weight |
| (a) | 1-5 |
| (b) | 15-25 |
| (c) | 10-20 |
| (d) | 40-70 |

The following example 2 exemplifies a lotion with a sunscreen component in the form of para-amino-benzoate:

| Example 2 | |
|---|---|
| Ingredient | Parts by Weight |
| (a) | 1-5 |
| (b) | 15-25 |
| (c) | 10-20 |
| (d) | 30-60 |
| para-aminobenzoate | 5-10 |

Perfume may be added in small quantities in order to attain an aesthetically pleasing fragrance of the product.

Ches 500 may be added, if water is used as an ingredient, in a small amount such as 1-5 parts to 10 parts, to stabilize the emulsion, as stated hereinabove.

As described hereinabove, the shaving lotion, according to the invention, may advantageously be applied to the skin by means of a roll-on applicator of substantially conventional construction, as shown on the drawing, FIGS. 1-6. The applicator 10 or 11 consists of a container 14 for the viscous lotion and has a neck 15 with edges 16 which grip a spherical roller 12 or an elongate roller 13 in a loosely fitting connection. The roller 12 or 13 has a rough textured surface, which when rolled over the skin, transfers a film of lotion from the container to the skin. Shaving of the skin may subsequently be carried out with a sharp blade in a conventional manner.

I claim:

1. A shaving and facial composition comprising in parts by weight:
   (1) wheat germ oil transesterificated with glycerine to form monglycerides, diglycerides and triglycerides, 30-40 parts;
   (2) cocoamide DEA used as an emulsifier, 15-20 parts;
   (3) oleth-2 polyethylene glycol ether of oleyl alcohol used as a surfactnat, 10-14 parts;
   (4) octyl hydroxystearate used as a refatting agent, 40-60 parts.

2. A shaving and facial composition according to claim 1 further comprising, 50-60 parts water and an emulsifier in the amount of 5-10% of total weight used as an emulsion stabilizer.

3. Composition according to claim 1 further comprising a sunscreening agent selected from the group consisting of para-aminobenzoate and rice bran oil.

4. Composition according to claim 1 further comprising perfume.

5. Composition according to claim 2 further comprising perfume.

6. Composition according to claim 5 further comprising a sunscreening agent selected from the group consisting of para-aminobenzoate and rice bran oil.

7. Composition according to claim 3 further comprising perfume.

8. Method of applying the anhydrous viscous, latherless multi-ingredient shaving composition of claim 1, the method which comprises the steps of:

pouring the viscous composition into a roll-on applicator;

rolling the applicator across the skin to transfer a film of the composition to the skin;

shaving the skin with a sharply hone razor blade.

9. Method of applying a viscous, latherless shaving composition including in parts by weight:

(1) wheat germ oil transesterificated with glycerine to form monglycerides, diglycerides and triglycerides, 30–40 parts;

(2) cocoamide DEA used as an emulsifier, 15–20 parts;

(3) oleth-2 polyethylene glycol ether of oleyl alcohol used as a surfactant, 10–14 parts;

(4) octyl hydroxystearate used as a refatting agent, 40–60 parts;

the method which comprises the steps of:

combining ingredients 1, 2, 3 and 4 by mechanical mixing, gently warming and stirring until a homogenous mixture is produced.

10. Method according to claim 9, further comprising:

adding 50–60 parts water and an emulsifier in the amount of 5–10% of total weight used as in emulsion stabilizer.

11. Method according to claim 9 further comprising:

adding a sunscreening agent selected from the group consisting of para-aminobenzoate and rice bran oil.

12. Method of applying an anhydrous viscous latherless shaving composition according to claim 8, the composition which comprises the ingredients, measured in parts by weight:

glycerine to form monglycerides, diglycerides and triglycerides, 30–40 parts;

cocoamide DEA used as an emulsifier, 15–20 parts;

oleth-2 polyethylene glycol ether of oleyl alcohol hydroxystearate used as a refatting agent, 10–14 parts.

* * * * *